US006548260B1

(12) United States Patent
Tewari

(10) Patent No.: US 6,548,260 B1
(45) Date of Patent: Apr. 15, 2003

(54) DETECTION OF PSA-α2-MACROGLOBULIN COMPLEX IN A BIOLOGICAL FLUID

(75) Inventor: Prakash Tewari, Mansfield, MA (US)

(73) Assignee: Bayer Corporation, Tarrytown, NY (US)

( * ) Notice: Subject to any disclaimer, the term of this patent is extended or adjusted under 35 U.S.C. 154(b) by 0 days.

(21) Appl. No.: 09/007,403

(22) Filed: Jan. 15, 1998

Related U.S. Application Data
(60) Provisional application No. 60/035,970, filed on Jan. 21, 1997, now abandoned.

(51) Int. Cl.$^7$ ........................ G01N 33/53; G01N 33/574
(52) U.S. Cl. ........................ 435/7.1; 435/7.23; 435/7.8; 435/7.92
(58) Field of Search ...................... 436/63, 64; 435/7.1, 435/7.23, 7.8, 7.92

(56) References Cited

U.S. PATENT DOCUMENTS

| | | | |
|---|---|---|---|
| 5,501,983 A | 3/1996 | Lilja et al. | ................... 436/518 |
| 6,174,858 B1 * | 1/2001 | Brady et al. | |

FOREIGN PATENT DOCUMENTS

| | | | |
|---|---|---|---|
| WO | 95/18381 | 7/1995 | ......... G01N/33/574 |
| WO | 97/02350 | 1/1997 | ........... C12N/15/57 |

OTHER PUBLICATIONS

Gelboin (Pharmacological Rev, 1993, 45: 413–453).*
Stenman et al (Cancer Res, 1991, 51: 222–226).*
*Monoclonal Antibody (F5) to Human Prostate Antigen*, Lawrence D. Papsidero, et al., Hybridoma, vol. 2, No. 2, 1983, Mary Ann Liebert, Inc., Publishers, pp. 139–147.
*Immunohistochemical Demonstration of Prostate–Specific Antigen in Metastases With the Use of Monoclonal Antibody F5*, Lawrence D. Papsidero, et al., publication Jul. 1, 1985, pp. 451–454.
*Prostate–Specific Antigen Domain of Human Prostate Specific Antigen Identified with Monoclonal Antibodies*, T. Ming Chu, et al, vol. 141, Jan.; The Journal of Urology, copyright 1989, pp. 152–156.
*Epitope Mapping of 53 Antibodies against Prostate–Specific Antigen*, L. Bellanger, et al, Tumor Biology 1999, pp. 18–23.
α$_2$ –*Macroglobulin and C1–Inactivator are Plasma Inhibotors of Human Glandular Kallikrein*; M.J. Heeb and F. Espana, Blood Cells, Molecules, and Diseases 1998, Article No. MD980209, pp. 412–419.
*A Complex between Prostate–specific Antigen and α$_1$–Antichymotrypsin Is the Major Form of Prostate–specific Antigen in Serum of Patients with Prostate Cancer: Assay of the Complex improves Clinical Sensitivity for Cancer*: Ulf–Hakan Stenman, et al. Cancer Research, Jan. 1, 1991, pp. 222–226.

*Characterization and immunological determination of the complex between prostate–specific antigen and α$_2$–macroglobulin*, Zhang, et al, Clinical Chemistry, 1998, Enzymes and Protein Markers, pp. 2471–2479.
*Tandem–R PSA, Immunoradiometric Assay For the quantitative measurement of Prostate–Specific Antigen (PSA) in human Serum*, Beckman Coulter, pp. 1–5.
ACS:s180, Bayer, PSA, manufacturer's instructions.
Certificate of Analysis, Dako, Mar. 1994, product insert.
Certificate of Analysis, Athens Research and Technology, Inc., Mar. 9, 1998, product insert.
Barrett et al, 1979, Biochem J., 181:401–418.
Sottrup–Jensen L., 1989, J. Biol. Chem., 264:11539–11542.
Otto et al, 1998, J. Urology, 259:297–303.
Birkenmeier, G., 1993, J. Immunol. Meth., 162:59–67.
Chen et al., "Addition of Purified PSA to Female Serum: Studies on the Relative Inhibition by α$_2$–macroglobulin and α$_1$–antichymotrypsin," *Journal of Urology* 156:1357–1363 (1996).
Christenson et al., "Enzymatic activity of prostate–specific antigen and its reactions with extracellular serine proteinase inhibitors," *European Journal of Biochemistry* 194:755–763 (1990).
España et al., "Quantitative Immunoassay for complexes of prostate–specific antigen with α$_2$–macroglobulin," *Clinical Chemistry* 42:4, 545–550 (1996).
Heeb et al., "Prostate Specific Antigen–α$_2$–Macroglobulin Complexes In Prostate Cancer Patient Sera," *Biochemistry and Molecular Biology International* 37:917–923 (1995).
Honda et al., "Prostate–specific antigen concentrations in serum in acute illnesses," *Clinical Chemistry* 42:11, 1785–1788 (1996).
Malm et al., "Biochemistry of Prostate Specific Antigen, PSA," *Scandinavian Journal of Clinical and Laboratory Investigation* 55:15–22 (1995).
Mansikka–Savolainen et al., "Development of immunofluorometric assay for in vitro prostate specific antigen–alpha2–macroglobulin complex," Proceedings of the XVI International Congress of Clinical Chemistry, A452, 159 (1996).
McGarvey et al., "In Situ Hybridization Studies of α$_2$–Macroglobulin Receptor and Receptor–Associated Protein in Human Prostate Carcinoma," *The Prostate* 28:311–317 (1996).

(List continued on next page.)

Primary Examiner—Susan Ungar
(74) Attorney, Agent, or Firm—Weingarten, Schurgin, Gagnebin & Lebovici LLP

(57) ABSTRACT

The present invention provides methods for detecting and quantitating PSA-α2-macroglobulin complexes in the sera of patients at risk for prostate cancer. Methods for detecting and monitoring prostate cancer in a patient by determining the serum level of the complex also are described, as are kits for performing the methods.

13 Claims, 8 Drawing Sheets

OTHER PUBLICATIONS

Tewari et al., "Immunological Characterization and quantitation pf prostate specific antigen–α2–macroglobulin complex in prostate cancer patient sera," *Clinical Chemistry* 41:S226 (1995) [Abstract].

Tewari, Prakash C., "Molecular and Immunochemical Analysis of PSA, PSA–α1–antichymotrypsin and PSA–α2–macroglobulin complexes in the Sera of Prostate Cancer Patients," First International Consultation on Prostate Cancer, Monaco (Jun. 21, 1996).

Tewari et al., "Multiple Forms of Prostate Specific Antigen and the Influences of Immunoassays Design on their Measurement in Patient Serum," *Journal of Clinical Ligand Assay* 18:186–196 (1995).

Towbin et al., "Immunoblotting and Dot Immunobinding—Current Status and Outlook," *Journal of Immunological Methods* 72; 313–340 (1984).

Zhou et al., "Multiple Forms of Prostate–Specific Antigen in Serum: Differences in Immunorecognition by Monoclonal and Polyclonal Assays," *Clinical Chemistry* 39/12, 2483–2491 (1993).

* cited by examiner

N/A

DETECTION OF PSA-α2-MACROGLOBULIN COMPLEX IN A BIOLOGICAL FLUID

This application claims the benefit of U.S. Provisional Application No. 60/035,970 filed Jan. 21, 1997, now abandoned.

BACKGROUND OF THE INVENTION

Prostate-specific antigen (PSA) is a kallikrein like serine protease secreted by the epithelial cells of the prostate gland. It is one of the predominant proteins present in prostatic fluid. Low levels of PSA are detected in all males, although the physiological function of PSA in the blood circulation still is not clear. Changes in anatomy of the prostate gland may lead to the diffusion of PSA into the blood circulation. Elevated PSA concentration in serum is indicative of several pathologic conditions including benign prostatic hyperplasia (BPH), prostatitis and prostate cancer.

If an active protease remains uncontrolled in circulation, it may potentially damage cellular components. The proteolytic activity of PSA in serum is inhibited by protease inhibitors such as alpha-1-antichymotrypsin (α1-ACT), alpha-2-macroglobulin (α2-M), and other acute phase proteins. The predominant form of PSA in prostate cancer patient serum (~86% of total), as detected by the current immunoassays, is complexed with α1-ACT. The rest of the immunologically detectable PSA exists as an enzymatically non-reactive free form. In most prostate cancer patients, the PSA level is consistently higher than that of normal males. As PSA is produced primarily by the prostate gland, its serum value in prostate cancer patients is reduced to virtually non-detectable levels after successful radical prostatectomy. Therefore, PSA is currently recognized as an important in vitro diagnostic parameter for monitoring patients with prostate cancer in order to detect residual disease and recurrence after therapeutic and/or surgical intervention.

α2-M possesses the ability to inhibit proteineases displaying different specificities and catalytic mechanisms. Cleavage of a peptide bond within the bait region triggers a conformational change that encages the proteinase and sterically hinders its access to larger substrates and active-site-directed inhibitors, as well as to antibodies. It has been demonstrated that α2-M is the major inhibitor of proteolytic activity of PSA. Honda et al., Clin. Chem. vol. 42, pp 1785–1788 (1996). The current generation of total PSA assays do not recognize PSA-α2-M complex, and technical difficulties in measuring this complex in patient's serum have undermined the clinical significance of PSA-α2-M complex. Currently the proportion of free to total PSA is being used to discriminate BPH and prostate cancer. A higher proportion of free PSA is indicative of a high probability of BPH.

Prostate cancer is the second leading cause of death in the U.S. male population. Currently PSA is used for the early diagnosis and monitoring of prostate cancer. There is significant overlap between the PSA serum level values obtained from patients afflicted with benign conditions, such as benign prostatic hyperplasia (BPH), and those afflicted with prostate cancer. Therefore, PSA alone cannot be used as a reliable parameter to a screen for prostate cancer, or to discriminate BPH from prostate cancer.

It is an object of the invention to provide methods and diagnostic compositions capable of accurately determining the levels of PSA-α2-macroglobulin complex in patient blood samples as a reliable indicator of the presence and/or the stage of prostate cancer.

SUMMARY OF THE INVENTION

The present invention is based on the discovery by Applicants that PSA-α2-M complexes exist in clinically significant concentrations in fluid samples drawn from individuals afflicted with prostate cancer. Applicants for the first time have shown that these complexes are present in vivo, and have detected the presence and concentration of the complexes in the sera of prostate cancer patients using molecular sieve chromatography, Western blot analysis and a two-site immunoassay. Applicants have demonstrated that as much as 60% of the total circulating levels of PSA exist as the PSA-α2-M complex in prostate cancer patients. Measurement of the levels of PSA-α2-M complexes in biological fluids provide a better indicator of the presence of prostate cancer, as well as an earlier indication of malignancy, than measuring the PSA-ACT complex or free PSA. Measurement of the PSA-α2-M complex can detect false negatives which occur using PSA tests, and improve clinical sensitivity. Measurement of PSA-α2-M complexes also can be used in screening for and diagnosing prostate cancer, to differentiate between benign conditions such as BPH and prostate cancer, for the early detection of prostate cancer, as an indicator of metastases and for differentiating between latent and potentially aggressive prostate cancer.

In one aspect, the invention comprises methods for detecting the presence and/or determining the quantity of PSA-α2-M complex in a biological fluid of a subject. The method generally comprises contacting the sample of biological fluid with one or more binding proteins that specifically bind to the PSA-α2-M complex, and detecting the binding proteins bound to said complex. The subject preferably is a human, and the biological fluid preferably is blood serum or plasma, or a fraction thereof. In a preferred embodiment, the method is a two-site immunoassay. The immunoassay protocol comprises combining serum from a subject suspected of having or at risk for prostate cancer with a binding protein specific for PSA under conditions sufficient to promote binding of the binding protein to PSA in the sample. The mixture then is combined with a second binding protein which is specific for α2-M in the sample. The amount of PSA-α2-M in the serum sample then can be determined by detecting any material to which has bound both binding proteins.

The invention further comprises methods for detecting the presence of or determining the quantity of PSA-α2-M complex in a biological fluid of a subject using a Western blot method. In this embodiment, the biological fluid, or fraction thereof, is solubilized with a detergent, preferably sodium dodecyl sulfate (SDS), then applied to gels. Electrophoresis is performed to separate the components. The separated components then are transferred to a solid substrate, such as a nitrocellulose membrane. In a preferred embodiment, a blocking agent is applied to the substrate to block non-specific binding. The components then are immunodetected with monoclonal antibodies against PSA. The amount of the complex present then can be quantitated, for example, using quantitative densitometry.

In another aspect, the invention comprises methods for detecting the presence of prostate cancer in a subject by detecting the presence of PSA-α2-M complex in a biological fluid of a subject. In preferred embodiments of these methods, the PSA-α2-M complex is detected using either the Western blot method or the immunoassay method described above.

The invention further comprises methods for differentiating between benign prostate conditions and prostate cancer, or to determine the stage of prostate cancer. This method comprises quantitating the amount of PSA-α2-M complex in the biological fluid of a subject, and correlating the level of the complex with the stage of the condition or cancer. In preferred embodiments, the amount of complex in the biological fluid is determined by Western blot or immunoassay methods. In a particularly preferred embodiment, the serum levels of PSA-α2-M complex are determined by obtaining a serum sample from an individual afflicted with or at risk for prostate cancer, combining the serum sample with a first conjugate comprising a PSA-specific binding protein and a solid phase under conditions sufficient to induce reaction between the first conjugate and PSA in the sample. The mixture formed after this step then is contacted with a second conjugate comprising a binding protein specific for α2-M in the sample and a detectable moiety under conditions sufficient to induce reaction between the second conjugate and α2-M in the sample. The solid phase, which at this point is attached to a reaction product comprising PSA specific binding protein, PSA-α2-M complex and α2-M-specific binding protein with a detectable moiety, is separated from the reaction mixture. The amount of PSA-α2-M complex then can be determined based on the amount of detectable moiety.

Applicants have found that substantial concentrations of PSA-α2-M complex are present in the sera of prostate cancer patients. The amount of PSA-α2-M complex is indicative of the stage or aggressiveness of the cancer. Thus, in addition to detecting the presence of prostate cancer, another aspect of the invention comprises methods for determining the stage of any cancer which is detected, for monitoring the progress of prostate cancer in a patient, and for differentiating between prostate cancer and benign states, such as BPH.

The invention further comprises kits for performing the methods. In one embodiment, the kit comprises, at a minimum, a first conjugate comprising a PSA-specific binding protein and a separable tag or solid phase; and a second conjugate comprising a binding protein which is specific for α2-M and a detectable moiety. The kit optionally may contain various reagents and containers, or other components useful for carrying out the method.

The present invention provides improved methods and kits for detecting the presence of, monitoring, and determining the stage of prostate cancer in an individual based on the discovery that the presence and/or amount of PSA-α2-M complex in the biological fluids of a subject is indicative of the presence and stage of prostate cancer. The methods and kits of the invention also provide a means to distinguish between prostate cancer and a benign prostate condition, such as BPH.

DETAILED DESCRIPTION

Figure 1:
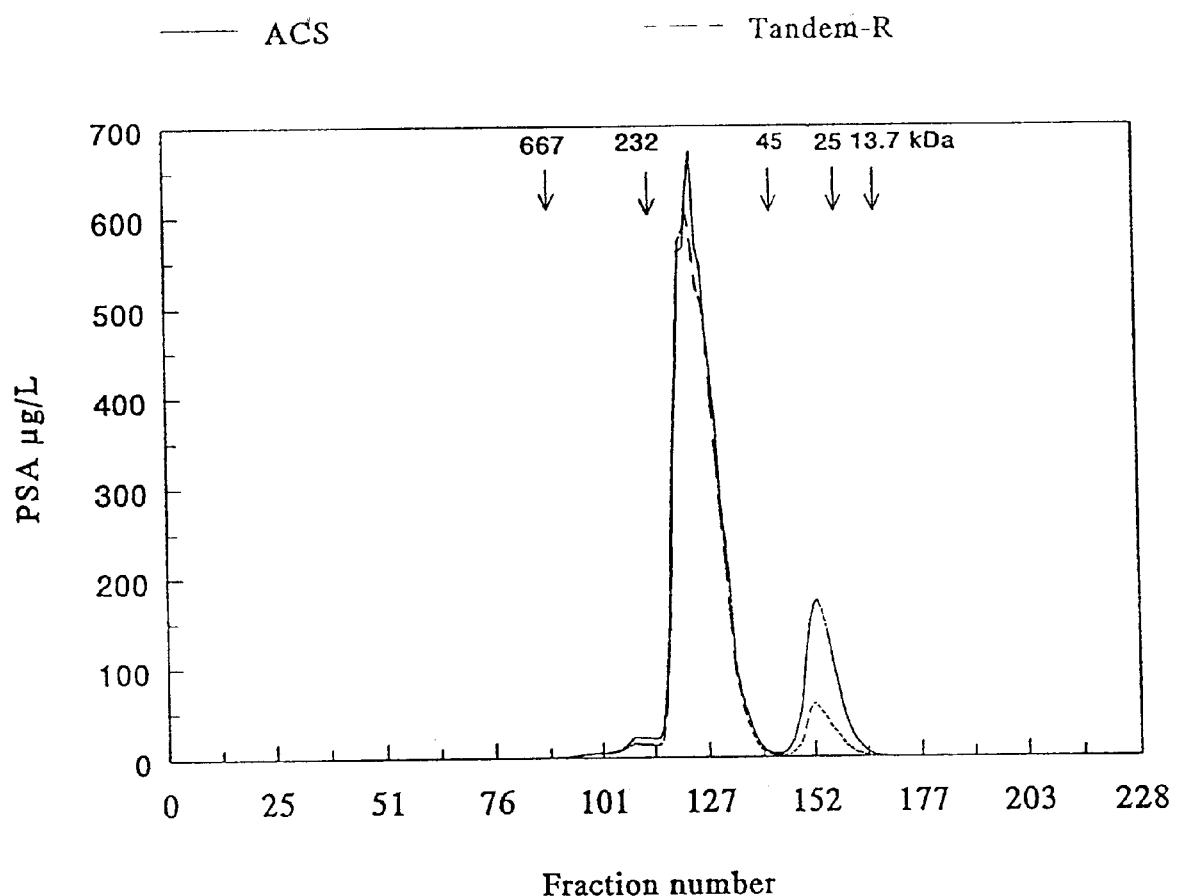
FIG. 1 is a graph showing the chromatographic elution profile of PSA in prostate cancer patient serum.

Encapsulation of PSA by α2-macroglobulin (α2-M) renders PSA inaccessible to two-site immunometric assays. Although PSA complexed with α2-M is immunologically reactive, its clinical significance has not been evaluated due to technical difficulties in its detection and quantification. Using molecular sieve chromatography, Western blot analysis, and immunoassays for PSA, Applicants demonstrated the presence of high molecular weight PSA-α2-M complexes in the sera of all prostate cancer patients.

Molecular sieve chromatography was used to characterize PSA-α2-macroglobulin complex, and to qualitatively confirm the molecular weight of the native molecule. Sera were obtained from several patients afflicted with prostate cancer. Using molecular sieve chromatography, the PSA-α2-M complex was chromatographically isolated as a 720 kDa complex. The fractions containing protein molecules of more than 700 kDa molecular weight were further probed on the Western blot the same way as whole intact serum. After SDS treatment these more than 700 kDa molecules broke down into subunits ranging from 270 to 360 kDa. Immunoreactive PSA was isolated at Mr~300 kDa, indicating the breakdown of α2-M from a tetrameric structure into dimers. A similar profile was seen for control PSA-α2-M complexes prepared in vitro by combining purified α2-M and PSA.

Applicants performed quantitative analysis of the chromatographically purified PSA-α2-M complexes using Western blot analysis and scanning densitometry. The results of this analysis, shown in Table 1, reveal that from about 35 to about 59% of the total circulating PSA in the sera of prostate cancer patients is present as PSA-α2-M complex. This is the first method which quantifies and demonstrates that a significant quantity of PSA complexed to α2-M exists in the blood sera of prostate cancer patients. Applicants found that the level of PSA-α2-M complex in the sera correlated to the stage of the cancer. Thus, low serum levels of PSA-α2-M complex are indicative of benign prostate disease or early stage cancer, and high levels of PSA-α2-M complex indicate advanced prostate cancer.

TABLE 1

Percentage of Different Forms of PSA in Prostate Cancer Patient Sera

| PSA Forms | Prostate Cancer Patient #1 | Prostate Cancer Patient #2 | Prostate Cancer Patient #3 | Mean |
|---|---|---|---|---|
| Free PSA | 18.1 | 9.9 | 9.9 | 12.6 |
| PSA-ACT | 46.6 | 30.8 | 44.9 | 40.8 |
| PSA-α2-M | 35.3 | 59.2 | 45.2 | 46.6 |

In one aspect, the invention comprises methods for detecting the presence and/or determining the quantity of PSA-α2-M complex in a biological fluid of a subject. The method generally comprises contacting the sample of biological fluid with one or more binding proteins that specifically bind to the PSA-α2-M complex, and detecting the binding proteins bound to said complex. In a preferred embodiment, the method is a two-site immunoassay. The immunoassay protocol comprises combining serum from a subject suspected of having or at risk for prostate cancer with a binding protein specific for PSA under conditions sufficient to promote binding of the binding protein to PSA in the sample. The binding protein preferably is an anti-PSA monoclonal antibody. For this purpose, an anti-PSA antibody designated F5-A-1/22.8.13 (ATCC HB 8051), or other antibodies to PSA can be used. The mixture then is combined with a second binding protein which is specific for α2-M in the sample. The second binding protein preferably is an affinity purified anti-α2-M monoclonal or polyclonal antibody. Suitable anti-α2-M antibody reagents are commercially available, for example from Dako A/S, Copenhagen, Denmark and Athens Research and Technology, Inc. (Athens, Ga.). The amount of PSA-α2-M in the serum sample then can be determined by detecting any material to which is bound both binding proteins. At least one of the binding proteins preferably is labeled with a detectable moiety, such as a chemiluminescent compound or a radioactive compound. Any detectable label can be used in the present methods.

Figure 6:
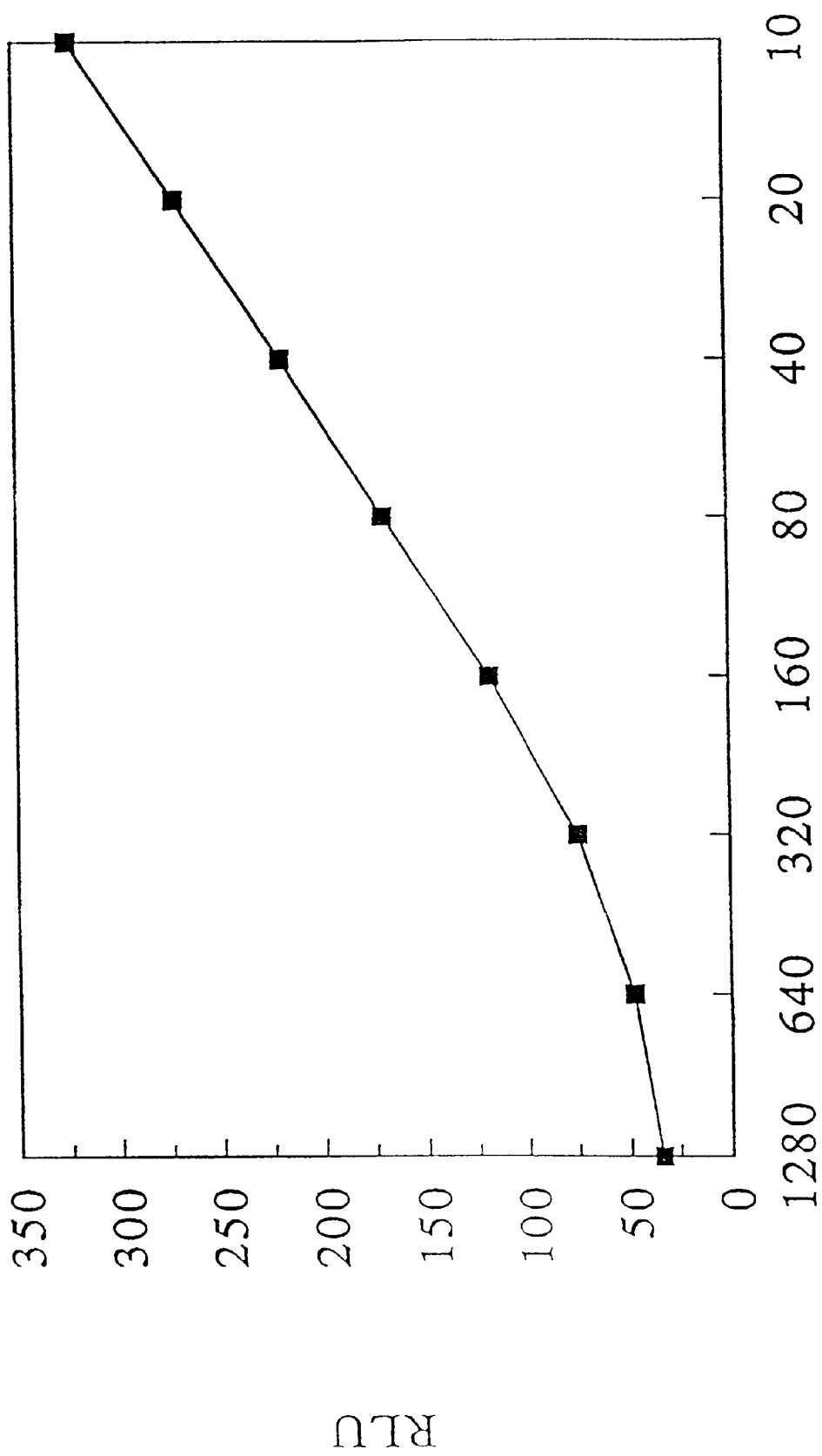
FIG. 6 is a graph illustrating the dose response of an immunoassay for PSA-α2-M, in terms of relative light units (RLU), in thousands, vs. the PSA-α2-M dilution factor.

The invention further comprises methods for detecting the presence of or determining the quantity of PSA-α2-M complex in a biological fluid of a subject using a Western blot method. In this embodiment, the biological fluid, or fraction thereof, is solubilized with a detergent, preferably sodium dodecyl sulfate (SDS), then applied to gels. Electrophoresis is performed to separate the components. The separated components then are transferred to a solid substrate, such as a nitrocellulose membrane. The components then are immunodetected with monoclonal antibodies against PSA, such as the antibodies described above. The amount of the complex present then can be quantitated, for example, using quantitative densitometry. (See FIG. 6 for a typical dose response of PSA-α2-M in terms of relative light units (RLU) in thousands vs. the PSA-α2-M dilution factor.)

In a preferred embodiment, a blocking agent is applied to the substrate to block non-specific binding. Any blocking agent which is effective for reduction of non-specific binding can be used. A blocking agent which is particularly effective for this purpose is Super Block, which is commercially available from Scytek Laboratories (Logan, Utah).

The sample may be pretreated prior to the immunoassay or Western blot methods. Pretreating may cause the PSA epitope in the PSA-α2-M complex to be more exposed, and therefore more available for binding. In a currently preferred embodiment of the methods of the invention, the pretreating step comprises warming the fluid sample and contacting it with a detergent, such as SDS. Other detergents may be used for this purpose.

In another aspect, the invention comprises methods for detecting the presence of prostate cancer in a subject by detecting the presence of PSA-α2-M complex in a biological fluid of a subject. In preferred embodiments of these methods, the PSA-α2-M complex is detected using either the Western blot method or the immunoassay method described above.

The invention further comprises methods for differentiating between benign prostate conditions and prostate cancer, or to determine the stage of prostate cancer. This method comprises quantitating the amount of PSA-α2-M complex in the biological fluid of a subject, and correlating the level of the complex with the stage of the condition or cancer. In preferred embodiments, the amount of complex in the biological fluid is determined by Western blot or immunoassay methods. In a particularly preferred embodiment, the serum levels of PSA-α2-M complex are determined by obtaining a serum sample from an individual afflicted with or at risk for prostate cancer, combining the serum sample with a first conjugate comprising a PSA-specific binding protein and a solid phase under conditions sufficient to induce reaction between the first conjugate and PSA in the sample. The solid phase used in the conjugates can be any solid material which will bind the specific binding proteins and permit the reaction product formed during the process to be removed from the reaction mixture. Solid phases may include, for example, magnetic particles, membranes, polymeric supports or other material having the desired characteristics. Magnetic particles are preferred for use in the present invention. The mixture formed after this step then is contacted with a second conjugate comprising a binding protein specific for α2-M in the sample and a detectable moiety under conditions sufficient to induce reaction between the second conjugate and α2-M in the sample. The solid phase, which at this point is attached to a reaction product comprising PSA specific binding protein, PSA-α2-M complex and α2-M-specific binding protein with a detectable moiety, is separated from the reaction mixture. The amount of PSA-α2-M complex then can be determined based on the amount of detectable moiety.

For all embodiments of the present invention, the subject preferably is a human, and the biological fluid preferably is blood serum or plasma, or a fraction thereof. The term "binding proteins" includes monoclonal and polyclonal antibodies, antibody fragments such as Fab, Fab', Fv, and single chain binding sites.

Applicants have found that substantial concentrations of PSA-α2-M complex are present in the sera of prostate cancer patients. The amount of PSA-α2-M complex is indicative of the stage or aggressiveness of the cancer. Thus, in addition to detecting the presence of prostate cancer, another aspect of the invention comprises methods for determining the stage of any cancer which is detected, for monitoring the progress of prostate cancer in a patient, and for differentiating between prostate cancer and benign states, such as BPH.

The invention further comprises kits for performing the methods. In one embodiment, the kit comprises, at a minimum, a first conjugate comprising a PSA-specific binding protein and a separable tag or solid phase; and a second conjugate comprising a binding protein which is specific for α2-M and a detectable moiety. The kit optionally may contain various reagents and containers, or other components useful for carrying out the method.

The present invention provides improved methods and kits for detecting the presence of, monitoring, and determining the stage of prostate cancer in an individual based on the discovery that the presence and/or amount of PSA-α2-M complex in the biological fluids of a subject is indicative of the presence and stage of prostate cancer. The methods and kits of the invention also provide a means to distinguish between prostate cancer and a benign prostate condition, such as BPH.

The invention is further illustrated by the following examples, which are not intended to be limiting in any way.

EXAMPLE 1

Molecular Sieve Chromatography

Superdex 200 gel was purchased from Pharmacia (Uppsala, Sweden). Molecular weight markers were purchased from Bio-Rad (Richmond, Calif.) and included catalase (240 kDa), bovine serum albumin (67 kDa), ovalbumin (43 kDa), chymotrypsinogen (25 kDa) and ribonuclease (14 kDa). The patient serum samples used in this and the following examples were drawn from patients having advanced forms of prostate cancer. The sera were obtained from M. D. Anderson Cancer Center (Houston, Tex.), Herbert A. Fritsche, Ph.D. and Stanford University Medical Center (Stanford, Calif.) and Thomas A. Stamey, M.D. Patient serum samples (200–500 μL) were fractionated at a flow rate of 0.1 mL/min on a 75×1.5 cm Superdex 200 gel packed in Bio-Rad Econo-columns. Fractions of 0.5 mL were collected and analyzed by the immunoassays. Elution buffers contained phosphate buffered saline (50 mM sodium phosphate, 150 mM sodium chloride, pH 6.9) with a 0.02% bovine serum albumin and 0.1% TRITON X-100. PSA in chromatographic fractions were measured by the following assays according to manufacturer's instructions: i) the ACS™ PSA assay (an automated, polyclonal/monoclonal immunochemiluminometric assay formatted for use on the Chiron's ACS:180® system, Chiron Diagnostics Corp., East Walpole, Mass.), and a HYBRITECH® TANDEM®-R PSA assay (a manual dual monoclonal immunoradiometric assay, Hybritech, Inc., San Diego, Calif.). Current PSA immunoassays cannot recognize and measure PSA-α2-macroglobulin complex.

FIG. 1 shows the chromatographic elution profile of PSA obtained from fractionation of the sera by the above method. Serum (0.2 mL) was applied to a Superdex 200 (75×1.5 cm) column. Fractions (0.5 mL) were collected at 0.1 mL/min flow rate and assayed for PSA by the Tandem-R and ACS PSA assays. This typical profile of a prostate cancer patient contains 16.5% free PSA and 83.5% PSA-alpha 1-antichymotrypsin complex.

EXAMPLE 2

Western Blot Analysis

In addition to PSA detection by standard immunoassay, some patient sera and selected fractions of serum (after molecular sieve chromatography) were subjected to Western blot analysis according to the methods of Towbin and Gorden. *J. Immunol. Methods* 72:313–340 (1984). Following solubilization in anionic detergent (SDS), samples were applied to Laemmli gels (1.5 mm thick) with a linear gradient. Electrophoresis was performed in a Bio-Rad Protean II xi system. Proteins were transferred to nitrocellulose membranes using Bio-Rad Trans-Blot cell. Membranes were blocked using Super Block (ScyTek Laboratories, P.O. Box 3286, Logan, Utah) to reduce non-specific protein binding and proteins were immunodetected with monoclonal antibodies against human PSA (F5-A-1/22.8.13; ATCC HB 8051). Visualization of the isolated bands was performed with horseradish peroxidase conjugated to anti-mouse IgG (Bio-Rad, Hercules, Calif.) and detected by enhanced chemiluminescence techniques using the ECL system (Amersham, Rockford, Ill.).

For quantitative densitometry of Western blot, the IS-1000 digital imaging system (Sun Bioscience Inc., 765 East Main St., Bradford, Conn.) was used. In this system a digital video camera captures the image of the Western blot and quantitate the staining density of every band. Using system's software distribution of PSA into different forms (free PSA, PSA-α1-antichymotrypsin and PSA-α2-macroglobulin complex) can be calculated.

EXAMPLE 3

Immunoassay Protocol for PSA-α2-M Complex

Serum                100 μL
                      +
Solid Phase (Anti PSA Mab:F5)
                     250 μL
                     ↓2 hour incubation 37° C.
                     Magnetic separation, 2 wash
Add Reagent (Sheep anti-α2-M polyclonal)
                     100 μL
                     ↓30 min incubation, 37° C.
                     Magnetic separation, 2 wash
Flash in Magic Lite Analyzer 2 (Chiron Diagnostics Corp., Medfield, MA)

PSA monoclonal antibody used in this assay: F5-A-1/22.8.13 ATCC HB 8051. The anti-α2-M polyclonal antibody used was affinity purified rabbit anti-human α2-macroglobulin available from Dako A/S (Copenhagen, Denmark). Other antibodies which recognize PSA α2-M complex can be used and are commercially available.

Serum samples were collected prior to prostate manipulation and stored at −20° C. or −80° C. until evaluation. Serum samples were obtained from the following institutions and investigators: MD Anderson Cancer Center (Houston, Tex.), Herbert A. Fritsche, Ph.D. and Stanford University Medical Center (Stanford, Calif.), Thomas A. Stamey, M.D. Serum samples used in this study were from advanced prostate cancer patients.

The above assay is useful for detecting the presence of prostate cancer in an individual by determining the amount of complex formed. Variations in the assay include (1) the use of a particle (possibly a magnetic particle) as the solid support, (2) binding of either PSA or α2M by the first binding protein, with the other entity being bound by the second binding protein, where either binding protein can be a polyclonal antibody or a monoclonal antibody, and (3) the possible use of a detectible moiety as the second binding protein.

EXAMPLE 4

Figure 2:
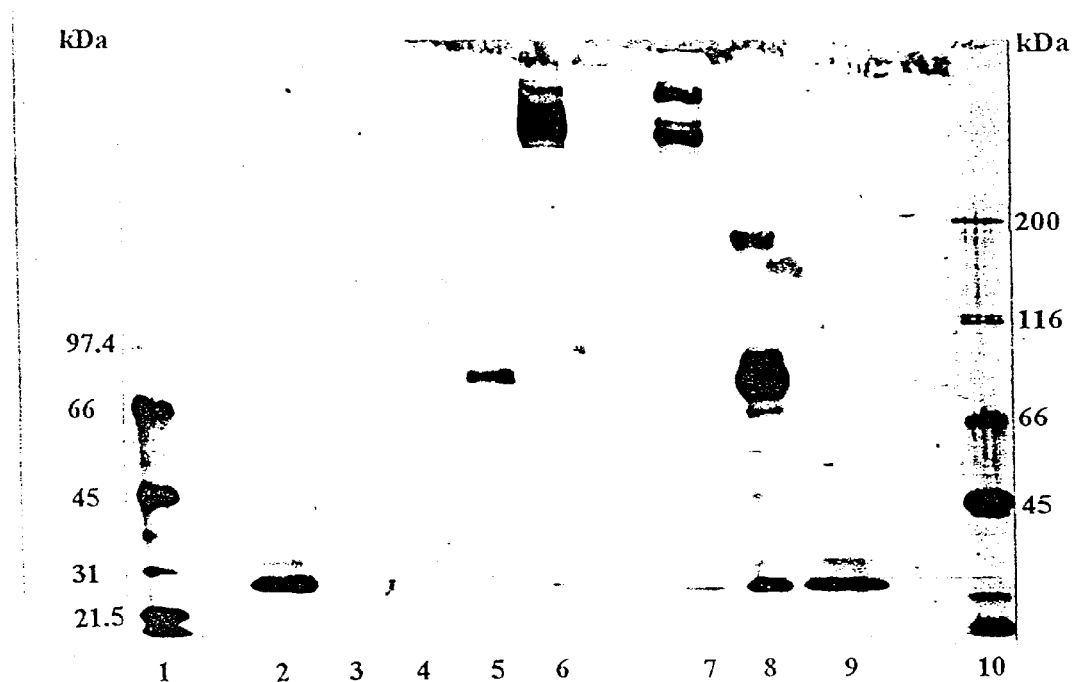
FIG. 2 is a Western Blot analysis of fractionated serum from prostate cancer patients, detected by an anti-PSA monoclonal antibody.

Using the protocol described in Example 2, Western Blot analysis of multiple forms of PSA was performed in the fractionated prostate cancer serum described in Example 1. Proteins were blotted onto nitrocellulose membranes after SDS PAGE (3–15% gradient) and were immunodetected with the anti-PSA MAB F5. The results are shown in FIG. 2: Lane 1, Low $M_r$ Markers; Lane 2, Stanford reference PSA; Lane 3, pure α1-ACT; Lane 4, pure α2-M; Lane 5, purified PSA-α1-ACT complex (prepared in vitro); Lane 6, purified PSA-α2-M complex (prepared in vitro); Lane 7, fraction #90; Lane 8, fraction #124; Lane 9, fraction #153; Lane 10, High $M_r$ Markers.

EXAMPLE 5

Figure 3:
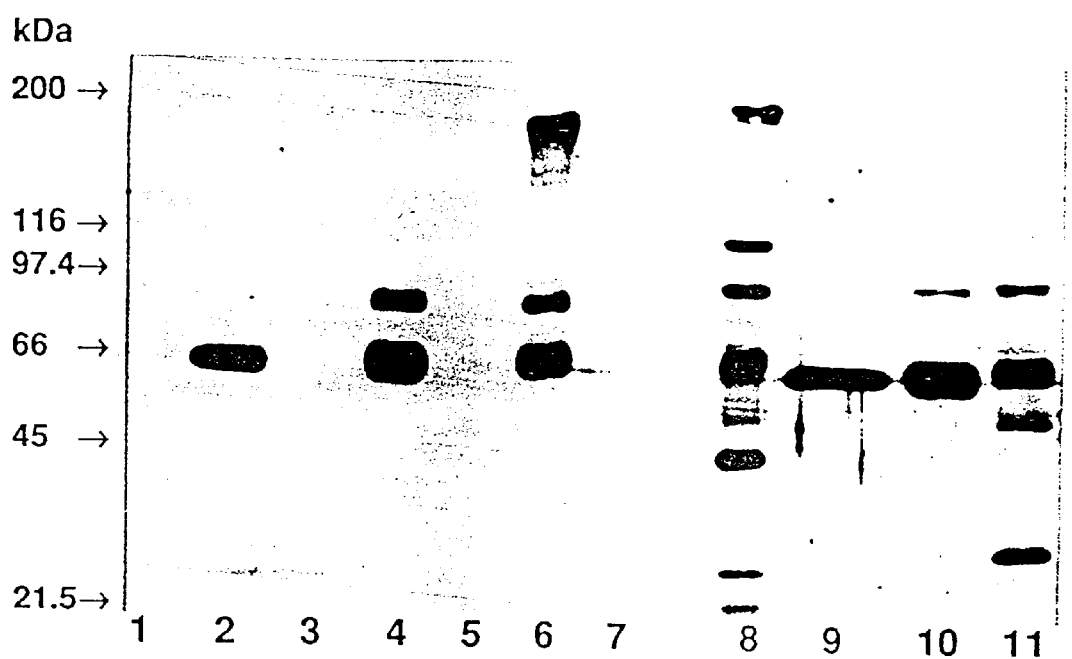
FIG. 3 is a Western Blot analysis of fractionated serum from prostate cancer patients detected by an anti-α1-ACT monoclonal antibody.

Using the protocol described in Example 2, Western Blot analysis of the fractionated prostate cancer serum described in Example 1 was performed. The separated proteins were immunodetected with anti-α1-ACT Mab. The results are shown in FIG. 3. Lane 1, Stanford reference PSA; Lane 2, pure α1-ACT; Lane 3 pure α2-M; Lane 4, PSA-α1-ACT complex, prepared in vitro, also contains unreacted free α1-ACT; Lane 5, fraction #90, ~700 kDa fraction; Lane 6, fraction #124, PSA-α1-ACT peak fraction; Lane 7, fraction #153, free PSA peak fraction; Lane 8, mol. wt. markers; Lane 9, reduced α1-ACT (same as in lane 2); Lane 10, reduced PSA-α1-ACT complex, prepared in vitro; Lane 11, reduced fraction #124, PSA-α1-ACT peak fraction.

EXAMPLE 6

Figure 4:
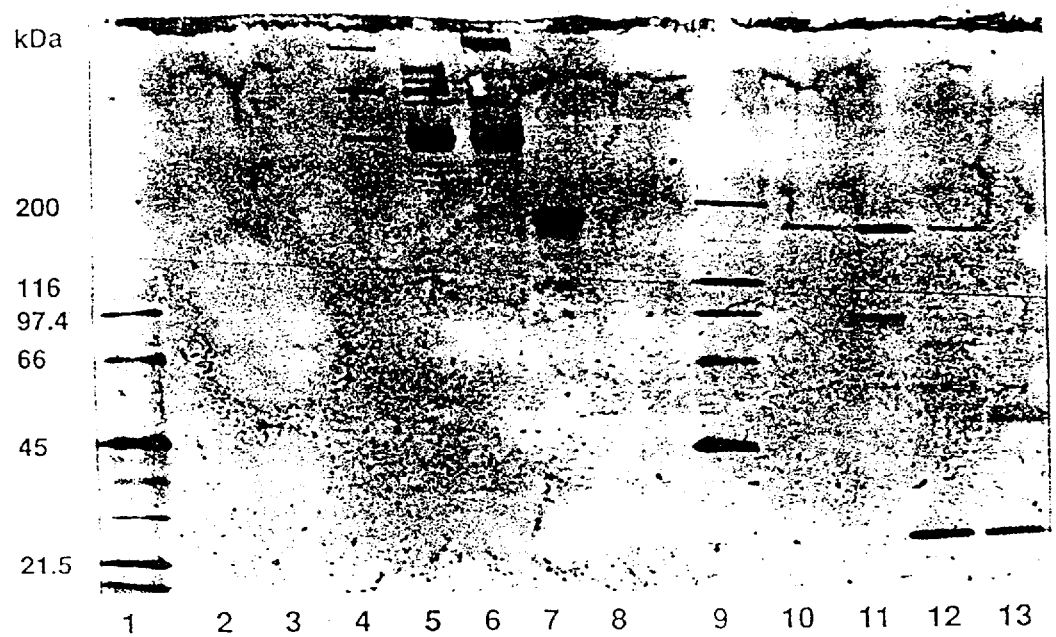
FIG. 4 is a Western Blot analysis of fractionated serum from prostate cancer patients detected with an anti-α2-M monoclonal antibody.

Using the protocol described in Example 2, Western Blot analysis of the fractionated prostate cancer serum described in Example 1 was performed. The separated proteins were immunodetected with anti-α2-M Mab. The results are shown in FIG. 4. Lane 1, mol. wt. markers; Lane 2, Stanford reference PSA; Lane 3, pure α1-ACT; Lane 4, pure α2-M; Lane 5, PSA-α2-M complex, prepared in vitro; Lane 6, fraction #92, ~700 kDa fraction; Lane 7, fraction #124, PSA-α1-ACT peak fraction; Lane 8 fraction #152, free PSA peak fraction; Lane 9, mol. wt. markers; Lane 10 reduced α2-M; Lane 11 reduced PSA-α2-M complex, prepared in vitro; Lane 12 reduced fraction #92, PSA-α2-M fraction from fractionated serum; Lane 13 reduced fraction #124.

EXAMPLE 7

Figure 5:
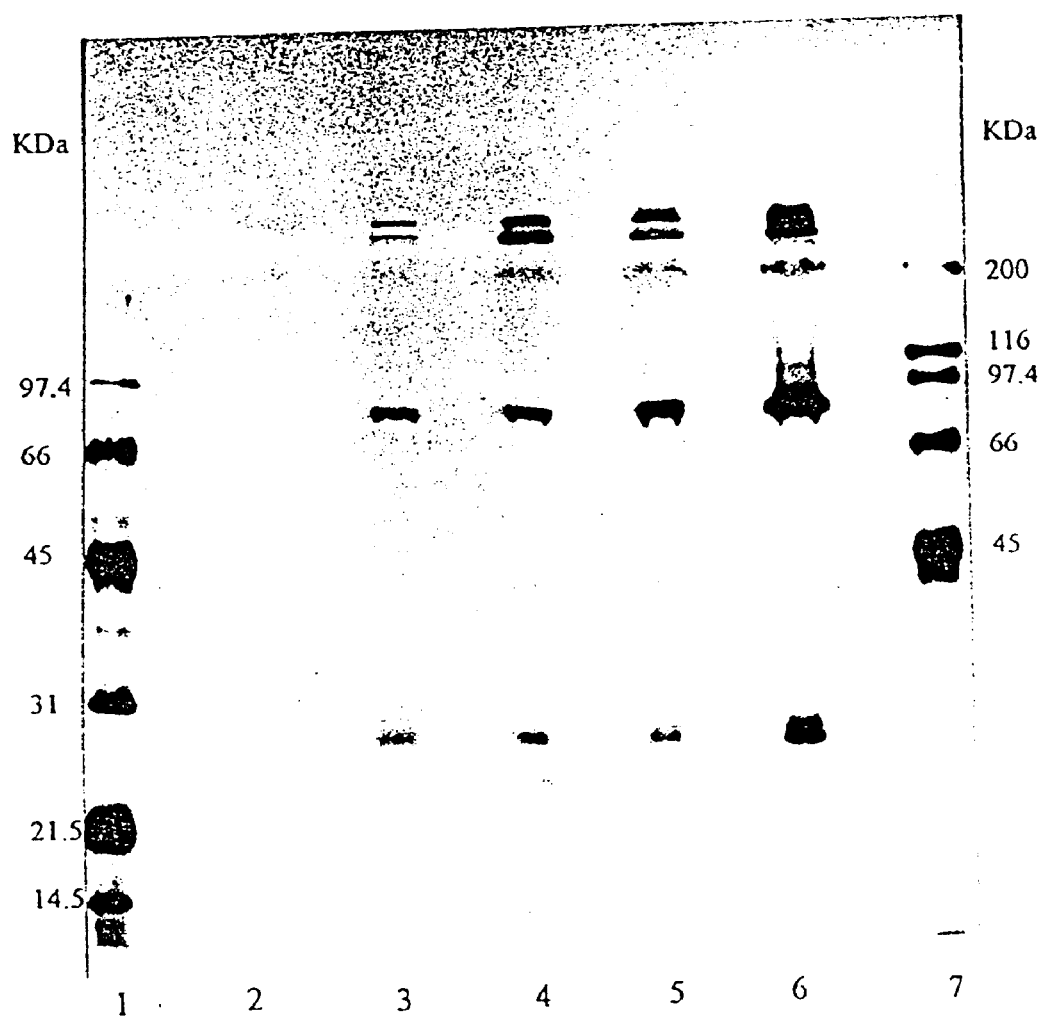
FIG. 5 is a Western Blot analysis of multiple forms of PSA in intact sera from prostate cancer patients detected with an anti-PSA monoclonal antibody.

Using the protocol described in Example 2, Western Blot analysis of multiple forms of PSA in prostate cancer intact sera was performed. Proteins were blotted onto nitrocellulose membranes after SDS PAGE (10–15% gradient) and were immunodetected with the anti-PSA Mab F5. The results are shown in FIG. 5. Lane 1, Low $M_r$ Markers; Lane 2, Normal Female Serum; Lanes 3 to 6=Prostate Cancer Sera with following PSA concentrations: Lane 3, 945 µg/L; Lane 4, 980 µg/L; Lane 5, 1540 µg/L; Lane 6, 1600 µg/L; Lane 7, High $M_r$ Markers.

EXAMPLE 8

Calibration of the PSA α2-M Immunoassay

Absence of any calibration material or immunoassay makes it very difficult to standardize and calibrate this assay. We have utilized a very simple concept to calibrate this assay in terms of PSA complexed with α2-M. We know that when free PSA is added to the normal female serum, it complexes with α2-M and resultant PSA-α2-M complex cannot be recognized or measured by current total PSA immunoassay. We prepared identical dilutions of purified free PSA in a protein buffer solution (phosphate buffered saline with 1% bovine serum albumin) and normal female serum. Both dilutions were incubated for 48 hours and total PSA was measured using ACS PSA2 immunoassay (Chiron Diagnostics, E. Walpole, Mass.). Dilution in female serum resulted in a lower total PSA value compared to total PSA value in protein buffer (As mentioned earlier this total PSA assay does not recognize PSA-α2-M complex). The difference in total PSA value was used to calculate quantity of PSA complexed with α2-M in the female serum.

Total PSA concentration in protein buffer and female serum were determined after incubation with identical quantities of free PSA for 48 hours:

Protein buffer 2.256 µg/mL

Female serum 0.839 µg/mL

Therefore PSA complexed with α2-M in the female serum was (2.256−0.839=1.417) 1.417 µg/mL. This stock solution with 1.417 µg/mL PSA bound to α2-M was used to prepare standards and used in PSA-α2-M complex immunoassay. This complex assay does not recognize or cross-react with the remaining non-reactive free PSA in the female serum.

EXAMPLE 9

Sample Pre-treatment to Expose PSA Epitope

The biochemical structure and mechanism of action of α2-M as a protease inhibitor is complicated as this molecule is composed of multiple subunits which entrap the protease (PSA) in a spring trap fashion. This trapping blocks the PSA molecule, making it unable to interact with antibody molecule unless first partially dissociated. We investigated different reagents and pH treatments to expose PSA epitope without destroying the PSA-α2-M complex. Serum sample treatment with Hydrochloric acid (HCl) or a low pH buffer was able to expose the PSA epitope.

It appears that low pH (less than 3) causes irreversible changes to structure of PSA-α2-M complex molecule. An immunoassay may not work at highly acidic pH (less than 3), therefore after an hour, acid is neutralized using an alkaline solution with high pH. After this treatment PSA-α2-M can be recognized and measured quantitatively using the PSA-α2-M immunoassay.

Example: 20 µL of 5N HCl was added to 500 µL of serum sample to bring the pH down to 1.5–3. Serum sample was kept at low pH between 1.5–3 for one hour at room temperature. After one hour 5 µL of 6N sodium hydroxide solution (NaOH) was added to neutralize acid and to bring the pH between 5.8 to 7. This acid/low pH treated serum allows to quantitate PSA-α2-M complex in the given sample.

Figure 7:
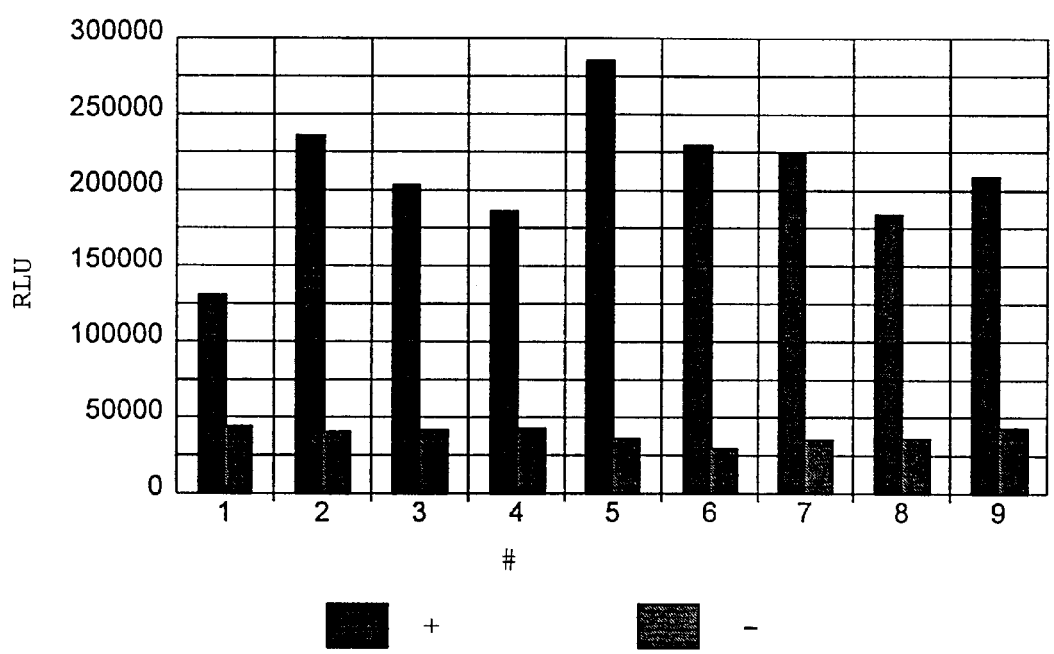
FIG. 7 is a graph showing the effect of pH treatment on the complex, in terms of relative light units (RLU) vs. serum sample number (#). Values are shown for pH treated serum (+) and untreated serum (−).
Figure 8:
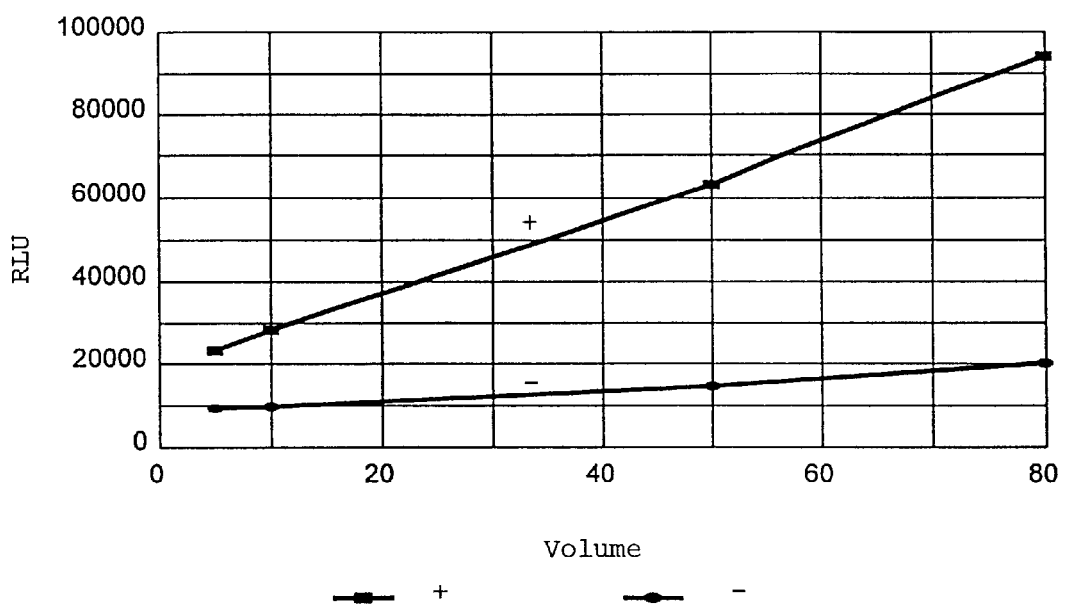
FIG. 8 is a graph showing the Dose Response after pH treatment, in terms of relative light units (RLU) vs. serum sample volume. Curves for both pH treated serum (+) and untreated serum (−) are shown.

See FIG. 7, where it is shown that PSA-α2-M complex immunoassay was able to recognize complex after pH treatment of the serum sample (samples identified by +) whereas signal (relative light units or RLU) from untreated serum sample (identified by −) was close to noise (background) level. Dose response significantly improved after pH treatment of the serum samples. (See FIG. 8)

EQUIVALENTS

Those skilled in the art will be able to determine equivalents to the specific embodiments described herein. All such equivalents are intended to be included within the scope of the following claims.

What is claimed is:

1. A method for detecting the presence or amount of PSA-α2-macroglobulin complex in blood drawn from an individual, said method comprising the steps of:

a) processing said blood to separate serum or plasma therefrom, b) exposing, in vitro, said serum or plasma of said individual to a pH pre-treatment that initially adjusts the pH to 3 or less, after which said serum or plasma is neutralized using an alkaline solution, whereby, after such exposure, a PSA epitope previously entrapped becomes available for specific binding, c) contacting said serum or plasma sample with an antibody or antibody fragment to PSA that binds PSA in PSA-α2-macroglobulin complex, said antibody or antibody fragment being immobilized on a solid support to form a PSA-α2-macroglobulin—solid phase conjugate;

d) isolating from said serum or plasma sample, said PSA-α2-macroglobulin—solid phase conjugate;

e) contacting said isolated PSA-α2-macroglobulin—solid phase conjugate with a labeling antibody or antibody fragment that binds α2-macroglobulin in said complex to form a labeled complexed antibody or antibody fragment thereof; and f) measuring the amount of said labeled antibody or antibody fragment bound to said complex to determine the amount of PSA-α2-macroglobulin complex.

2. The method of claim 1, wherein said solid phase comprises a magnetic bead.

3. The method of claim 1, wherein said detectable label comprises a chemiluminescent compound or a radioactive material.

4. The method of claim 1, wherein said α2-macroglobulin-specific antibody comprises an affinity purified antibody.

5. The method of claim 1, wherein in step (c) said antibody is a monoclonal antibody.

6. The method of claim 1, wherein in step (c) said solid support is a particle.

7. The method of claim 6, wherein said particle is a magnetic particle.

8. The method of claim 1, wherein in step (e) said labeling antibody or antibody fragment is conjugated to a detectable moiety.

9. The method of claim 1, wherein:
 in step (e) said labeling antibody or antibody fragment is conjugated to a detectable moiety and
 step (f) further comprises measuring the amount of said detectable moiety as an indication of the amount of labeling antibody or antibody fragment bound to said complex.

10. A method for pretreating a serum sample to be assayed for concentration of PSA-α2-M complex formed in vivo, wherein said method does not lead to the dissociation of said complex, said method comprising:
 a) adjusting the pH of said sample to approximately pH 1.5 to 3.0, by the addition of acid,
 b) allowing said sample with adjusted pH to remain at room temperature for about one hour, and
 c) after said one hour, adjusting the pH of said sample to approximately 5.8 to 7.0, by the addition of base.

11. The method of claim 9, wherein said acid is 5N HCl and said base is 6N sodium hydroxide.

12. A method for detecting the presence or amount of PSA-alpha2-macroglobulin complex in blood drawn from an individual, said method comprising the steps of:
 a) processing said blood to separate serum or plasma therefrom,
 b) treating said serum or plasma by
  (1) adjusting the pH of said sample to approximately pH 1.5 to 3.0, by the addition of acid,
  (2) allowing said sample with adjusted pH to remain at room temperature for about one hour, and
  (3) after said one hour, adjusting the pH said sample to approximately 5.8 to 7.0, by the addition of base,
 c) combining a sample of said serum or plasma from step (a) with a first conjugate comprising (i) a PSA-specific antibody or a PSA-specific antibody fragment thereof and (ii) a solid phase, under conditions sufficient to induce specific binding between said first conjugate and PSA in said sample to form a PSA-antibody solid phase conjugate;
 d) contacting said PSA-antibody solid phase conjugate formed in (b) with a second conjugate comprising (i) an α2-macroglobulin-specific antibody or an α2-macroglobulin-specific antibody fragment thereof and (ii) a detectable label, under conditions sufficient to induce specific binding between the second conjugate and α2-macroglobulin in said PSA-antibody solid phase conjugate in said serum or plasma to form an α2-macroglobulin-label complex;
 e) separating said solid phase conjugate from said sample; and
 f) detecting presence or amount of said label attached to said separated solid phase conjugate,
  wherein the presence or amount of PSA-α2-macroglobulin complex present is determined by correlating the results from step (f) to a calibration curve generated by the use of known amounts of PSA-α2-macroglobulin.

13. The method of claim 1, wherein said PSA specific binding protein comprises the antibody produced by cell line F5-A-1/22.8.13 (ATCC No. HB 8051).

* * * * *